United States Patent
Teysseyre et al.

(10) Patent No.: US 9,851,328 B2
(45) Date of Patent: Dec. 26, 2017

(54) COMPACT MICROELECTRONIC INTEGRATED GAS SENSOR

(71) Applicant: STMicroelectronics Pte Ltd, Singapore (SG)

(72) Inventors: Jerome Teysseyre, Ang Mo Kio (SG); Yonggang Jin, Singapore (SG); Suman Cherian, Kerala (IN)

(73) Assignee: STMICROELECTRONICS PTE LTD, Singapore (SG)

( * ) Notice: Subject to any disclaimer, the term of this patent is extended or adjusted under 35 U.S.C. 154(b) by 634 days.

(21) Appl. No.: 14/462,432

(22) Filed: Aug. 18, 2014

(65) Prior Publication Data

US 2016/0047774 A1 Feb. 18, 2016

(51) Int. Cl.
| | |
|---|---|
| G01N 27/28 | (2006.01) |
| G01N 27/403 | (2006.01) |
| G01N 27/413 | (2006.01) |
| G01N 27/406 | (2006.01) |
| G01N 27/407 | (2006.01) |
| H05K 1/18 | (2006.01) |

(52) U.S. Cl.
CPC ..... *G01N 27/4065* (2013.01); *G01N 27/4062* (2013.01); *G01N 27/4071* (2013.01); *G01N 27/4077* (2013.01); *H05K 1/185* (2013.01); *H05K 2201/09118* (2013.01); *H05K 2201/10151* (2013.01)

(58) Field of Classification Search
CPC .... G01N 27/028; G01N 27/045; G01N 27/28; G01N 27/304; G01N 27/403; G01N 27/413; G01N 27/414; G01N 27/4141; G01N 27/4148
See application file for complete search history.

(56) References Cited

U.S. PATENT DOCUMENTS

| | | | |
|---|---|---|---|
| 5,344,545 A | 9/1994 | Tsukada et al. | |
| 6,562,747 B2 | 5/2003 | Symons et al. | |
| 2007/0079597 A1* | 4/2007 | Wang | F01N 3/2066 60/277 |
| 2010/0170795 A1* | 7/2010 | Cowburn | G01N 27/404 204/406 |
| 2010/0252455 A1* | 10/2010 | Pratt | G01N 27/404 205/793 |
| 2011/0156177 A1* | 6/2011 | Merz | G01N 27/4148 257/414 |

* cited by examiner

*Primary Examiner* — Susan D Leong
(74) *Attorney, Agent, or Firm* — Seed IP Law Group LLP

(57) ABSTRACT

A compact microelectronic gas sensor module includes electrical contacts formed in such a way that they do not consume real estate on an integrated circuit chip. Using such a design, the package can be miniaturized further. The gas sensor is packaged together with a custom-designed Application Specific Integrated Circuit (ASIC) that provides circuitry for processing sensor signals to identify gas species within a sample under test. In one example, the output signal strength of the sensor is enhanced by providing an additional metal surface area in the form of pillars exposed to an electrolytic gas sensing compound, while reducing the overall package size. In some examples, bottom side contacts are formed on the underside of the substrate on which the gas sensor is formed. Sensor electrodes may be electrically coupled to the ASIC directly, or indirectly by vias.

19 Claims, 11 Drawing Sheets

COMPACT MICROELECTRONIC INTEGRATED GAS SENSOR

BACKGROUND

Technical Field

The present disclosure generally relates to miniature gas sensors, and in particular to chemireactive gas sensor modules integrated with microelectronic circuits in a single package.

Description of the Related Art

Miniature solid state gas sensors integrated with microelectronics allow construction of an "electronic nose" that can selectively detect the presence of various gases in a wide variety of applications. For example, such sensors can be used to detect toxic substances such as carbon monoxide (CO), methane ($CH_3$), or hydrogen gas ($H_2$) in a home or industrial environment. In another application, ethanol sensors can be provided within portable breathalyzers for use by law enforcement officers.

Chemireactive sensor materials for integration with microelectronics can be provided in various forms, including solids, liquids, gels, aerosols, gases, and the like. One example of a chemireactive material for use in microelectronic gas sensors is a solid electrolyte made of a zirconia-based mixture. Such solid electrolytes are used, for example, in automobile fuel control systems to sense the mixture of exhaust gases, in particular, oxygen, and then to adjust the air-to-fuel ratio to optimize combustion as described in U.S. Pat. No. 6,562,747. In response to a chemical reaction, electrolytic sensor compounds experience a change in conductivity that can be sensed by an electrode and transmitted as an electric current signal. Other types of electrolytes, for example, liquids or gels, can be incorporated into microelectronic gas sensors to measure an amount of a gas that is dissolved into a bodily fluid, e.g., oxygen dissolved in blood, as described in U.S. Pat. No. 5,344,545.

BRIEF SUMMARY

A compact microelectronic gas sensor package includes electrical contacts formed in such a way that they do not consume real estate on an upper surface of an integrated circuit chip. Various embodiments of a package integrated with a gas sensor module as disclosed herein use a liquid or gel type electrolytic gas sensing compound. The electrolytic gas sensing compound is contained either by a cap that fits over the substrate, or within the substrate itself. In some embodiments, the gas sensor module is packaged together with a custom-designed Application Specific Integrated Circuit (ASIC) that provides circuitry for processing sensor signals to identify gas species within a sample under test. By re-positioning the contacts, and eliminating the cap, the package can be miniaturized further, thus allowing circuit designers to increase the size of sensor electrodes in contact with the electrolytic material. The gas sensor electrodes may be electrically coupled to the ASIC directly, or indirectly, by vias. In some embodiments, electrical contacts are relocated to the backside of the substrate on which the gas sensor is formed. In some embodiments, the output signal strength of the sensor electrodes is enhanced by providing an additional metal surface area in the form of columns exposed to the electrolytic gas sensing compound, while reducing the overall package size.

BRIEF DESCRIPTION OF THE SEVERAL VIEWS OF THE DRAWINGS

In the drawings, identical reference numbers identify similar elements. The sizes and relative positions of elements in the drawings are not necessarily drawn to scale.

DETAILED DESCRIPTION

Figure 1A:
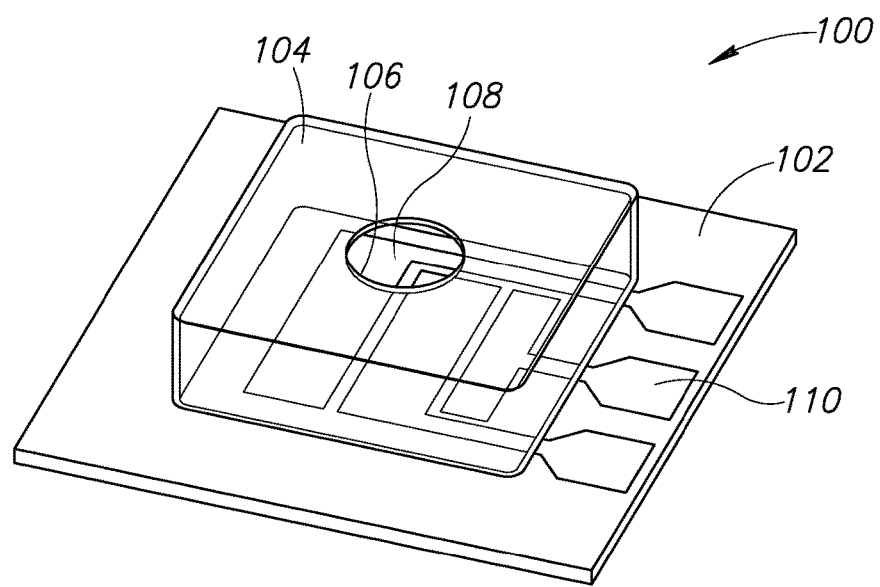
FIG. 1A is a top down perspective view of a prior art microelectronic gas sensor formed on a substrate, wherein electrical contacts occupy a large surface area of the substrate.

In the following description, certain specific details are set forth in order to provide a thorough understanding of various aspects of the disclosed subject matter. However, the disclosed subject matter may be practiced without these specific details. In some instances, well-known structures and methods of semiconductor processing comprising embodiments of the subject matter disclosed herein have not been described in detail to avoid obscuring the descriptions of other aspects of the present disclosure.

Unless the context requires otherwise, throughout the specification and claims that follow, the word "comprise" and variations thereof, such as "comprises" and "comprising" are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same aspect. Furthermore, the particular features, structures, or characteristics may be combined in any suitable manner in one or more aspects of the present disclosure.

Reference throughout the specification to integrated circuits is generally intended to include integrated circuit components built on semiconducting substrates, whether or not the components are coupled together into a circuit or able to be interconnected. Throughout the specification, the term "layer" is used in its broadest sense to include a thin film, a cap, or the like, and one layer may be composed of multiple sub-layers.

Reference throughout the specification to conventional thin film deposition techniques for depositing silicon nitride, silicon dioxide, metals, or similar materials include such processes as chemical vapor deposition (CVD), low-pressure chemical vapor deposition (LPCVD), metal organic chemical vapor deposition (MOCVD), plasma-enhanced chemical vapor deposition (PECVD), plasma vapor deposition (PVD), atomic layer deposition (ALD), molecular beam epitaxy (MBE), electroplating, electro-less plating, and the like. Specific embodiments are described herein with reference to examples of such processes. However, the present disclosure and the reference to certain deposition techniques should not be limited to those described. For example, in some circumstances, a description that references CVD may alternatively be done using PVD, or a description that specifies electroplating may alternatively be accomplished using electro-less plating. Furthermore, reference to conventional techniques of thin film formation may include growing a film in-situ. For example, in some embodiments, controlled growth of an oxide to a desired thickness can be achieved by exposing a silicon surface to oxygen gas or to moisture in a heated chamber.

Reference throughout the specification to conventional photolithography techniques, known in the art of semiconductor fabrication for patterning various thin films, includes a spin-expose-develop process sequence typically followed by an etch process. Alternatively or additionally, photoresist can also be used to pattern a hard mask (e.g., a silicon nitride hard mask), which, in turn, can be used to pattern an underlying film.

Reference throughout the specification to conventional etching techniques known in the art of semiconductor fabrication for selective removal of polysilicon, silicon nitride, silicon dioxide, metals, photoresist, polyimide, or similar materials includes such processes as wet chemical etching, reactive ion (plasma) etching (RIE), washing, wet cleaning, pre-cleaning, spray cleaning, chemical-mechanical planarization (CMP) and the like. Specific embodiments are described herein with reference to examples of such processes. However, the present disclosure and the reference to certain deposition techniques should not be limited to those described. In some instances, two such techniques may be interchangeable. For example, stripping photoresist may entail immersing a sample in a wet chemical bath or, alternatively, spraying wet chemicals directly onto the sample.

Specific embodiments are described herein with reference to sensor modules that have been produced; however, the present disclosure and the reference to certain materials, dimensions, and the details and ordering of processing steps are exemplary and should not be limited to those shown.

Figure 1B:
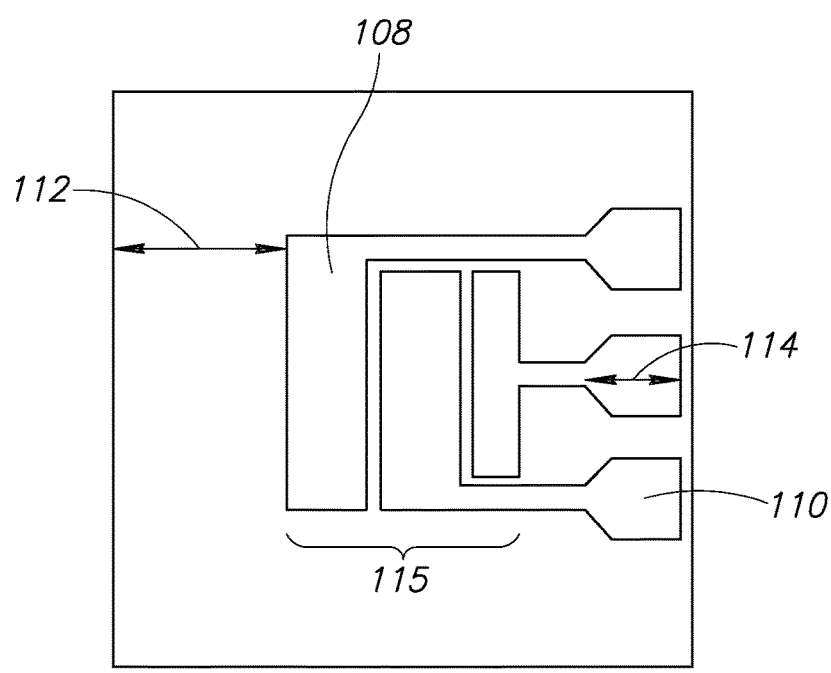
FIG. 1B is a layout of a top metal layer of the prior art microelectronic gas sensor shown in FIG. 1A.

FIGS. 1A and 1B show a conventional microelectronic gas sensor module 100 fabricated on an upper surface of a semiconductor substrate 102. The sensor module 100 is protected by a cap 104 having a lid in which there is an opening 106. The cap 104 provides containment for a liquid or gel-type gas sensing compound. The gas sensing compound is exposed to an ambient environment through the opening 106 in the cap 104. Sensor electrodes 108 (three shown) located underneath the gas sensing compound, on an upper surface of the substrate 102, are coupled to electrical contacts 110 that extend outside the cap 104. Each one of the contacts 110 provides electrical access to signals via a different one of the sensor electrodes 108, which are coupled to a sensor chip. The sensor chip is, for example, an application specific integrated circuit (ASIC) formed within the substrate 102 as an embedded die, which is not shown in the top view of FIG. 1A. Sensor data can be read, and the ASIC can be controlled, via the contacts 110.

One problem with the conventional microelectronic gas sensor module 100 is that the signal strength measurable as an electrical current at the sensor electrodes 108 is very small, in the range of only about 1-10 nA. It would therefore be advantageous to increase the surface area of the sensor electrodes 108 to capture more current from the gas sensing compound. Unfortunately, a significant portion of the surface area of the substrate 102 is occupied by the contacts 110. Furthermore, while the surface area of the substrate 102 around the perimeter outside the cap 104 provides space for the contacts 110, three sides of the perimeter are otherwise unoccupied. FIG. 1B shows the surface of the substrate 102 without the cap 104 in place. The total area of the substrate 102 as shown measures about 5 mm×5 mm, or 25 mm$^2$. It is clear from FIG. 1B that the sensor electrodes 108 occupy only a small fraction of the available surface area located in a center portion 115 of the substrate 102, while the perimeter that accommodates the contact width 114 accounts for a larger portion of the surface area of the gas sensor module 100. The center portion of the substrate 115 measures about 2.0 mm×2.4 mm or 4.8 mm$^2$, which represents only 20% of the total upper surface area of the substrate 102. Thus, the inventors have realized that if the contacts 110 could be re-located, 80% of the chip real estate could be recovered and used to accommodate larger sensor electrodes 108, which would substantially increase the signal strength of the gas sensor. Alternatively, if the contacts are re-located as suggested above, the sensor module can simply be shrunk to provide a reduced form factor.

Figure 2A:
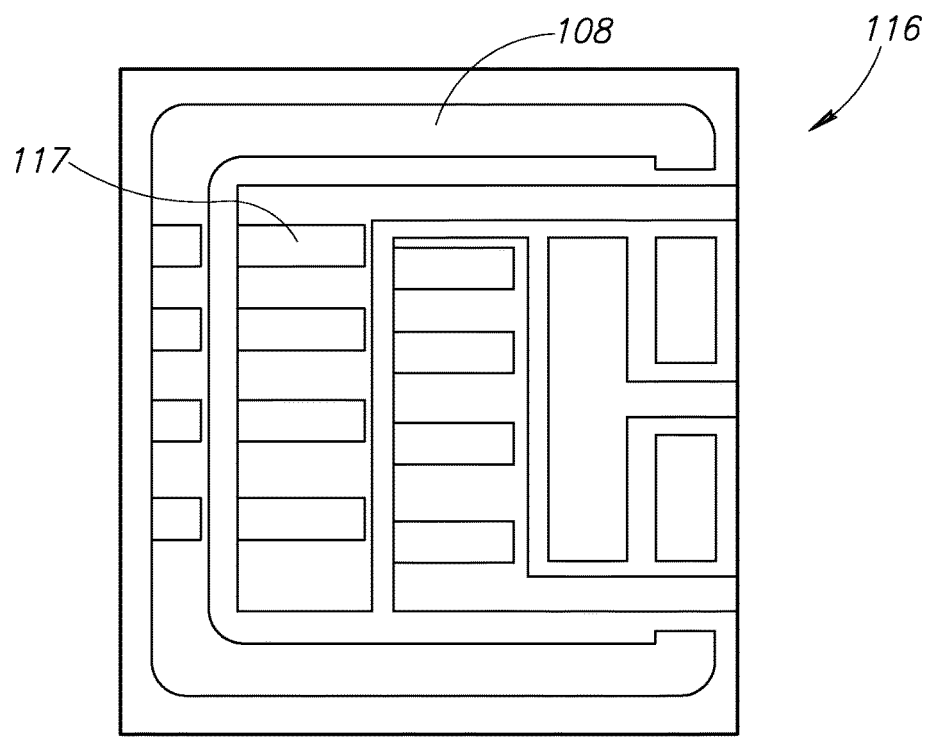
FIG. 2A is a layout of a top metal layer of a compact microelectronic gas sensor package according to one embodiment described herein.
Figure 2B:
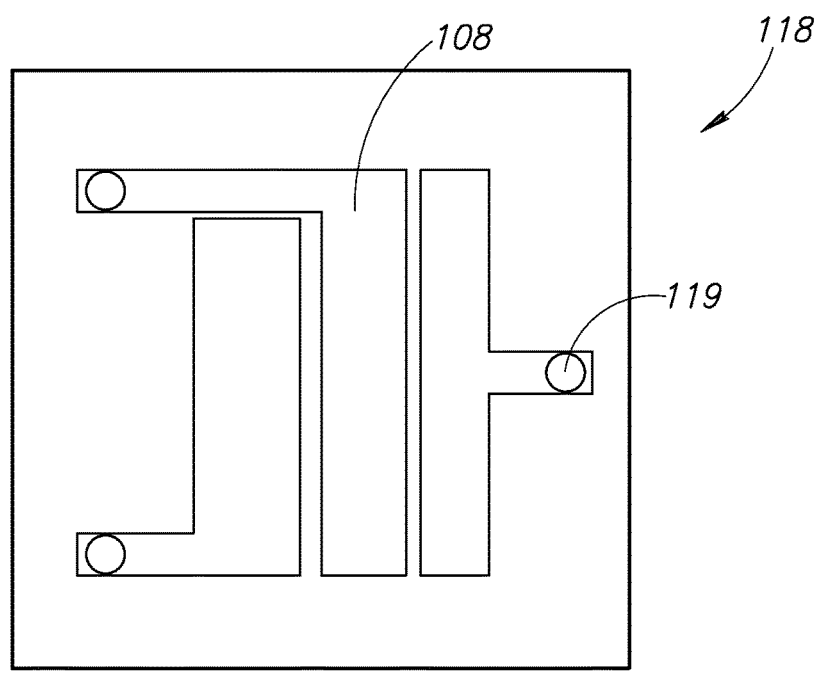
FIG. 2B is a layout of a top metal layer of a microelectronic gas sensor package according to a second embodiment described herein.

FIGS. 2A and 2B show top plan views of two embodiments of a compact microelectronic integrated gas sensor package, 116 and 118, respectively, formed on the substrate 102. For simplicity, the lid 104 is not shown. The compact microelectronic integrated gas sensor packages 116, 118 have layouts that feature top side electrical contacts 117a in place of the contacts 110. The top side electrical contacts 117a are formed directly on top of the sensor electrodes 108 so that the size of the overall package is reduced compared with the package shown in FIGS. 1A and 1B. Furthermore, the percentage of surface area used for the sensor electrodes 108 in the compact microelectronic integrated gas sensor package 116 is enhanced, thereby improving the sensor performance. The surface area of the compact microelectronic integrated gas sensor package 116 shown in FIG. 2A is about 3.0 mm×3.0 mm, or 9 mm$^2$, which represents about a 60% reduction in surface area compared with the conventional microelectronic gas sensor module 100. The compact microelectronic integrated gas sensor package 118 shown in FIG. 2B features top side electrical contacts 117a that are formed directly on top of the sensor electrodes 108, and that couple to the ends of vias 142 that extend vertically through the substrate 102 (shown later herein), so that the size of the overall package is reduced. The compact microelectronic integrated gas sensor package 118 shown in FIG. 2B is even smaller than the compact microelectronic integrated gas sensor package 116 shown in FIG. 2A. Additionally or alternatively, bottom side electrical contacts 117b can be formed underneath the substrate 102 (shown later herein) that couple to the underside of vias 142.

The electrical contacts 117a and 117b can be in the form of metallic pads and/or bumps made of gold, solder, or another appropriate metal material. Such similar to arrays of contacts typically formed on the surface of integrated circuit die packages for coupling to other chips or for mounting on printed circuit boards. The sensor electrodes 108 are desirably made of a high-conductivity metal such as gold, platinum, silver, or alloys thereof.

Figure 3:
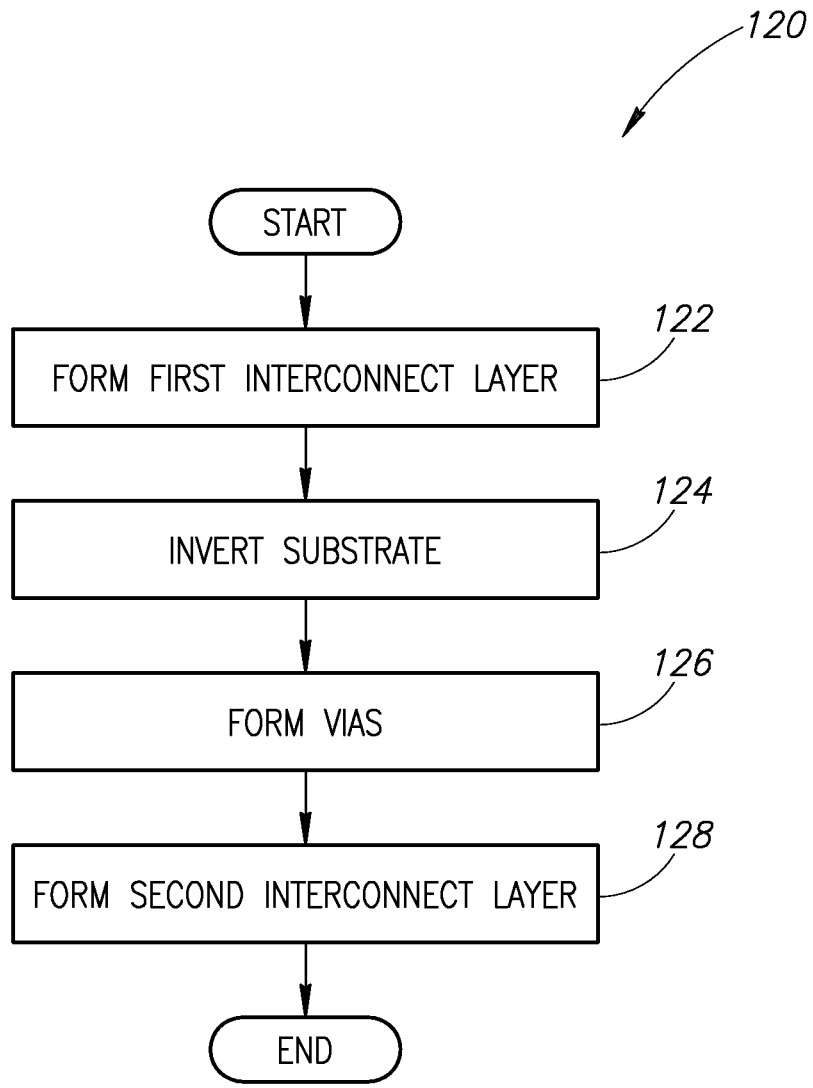
FIG. 3 is a high-level flow diagram summarizing a processing sequence for fabricating a compact microelectronic gas sensor package, according to one exemplary embodiment described herein.
Figure 4A:
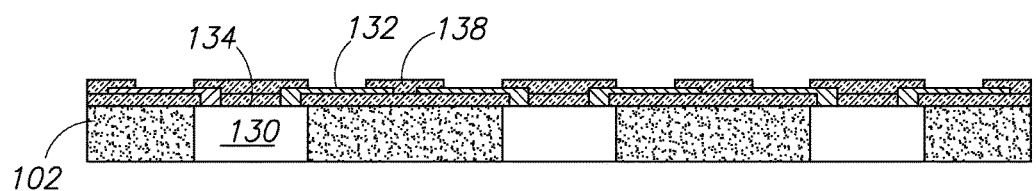
FIGS. 4A-4C are cross-sectional views of a microelectronic gas sensor package at various stages of fabrication, according to the processing sequence shown in FIG. 3.
Figure 4B:
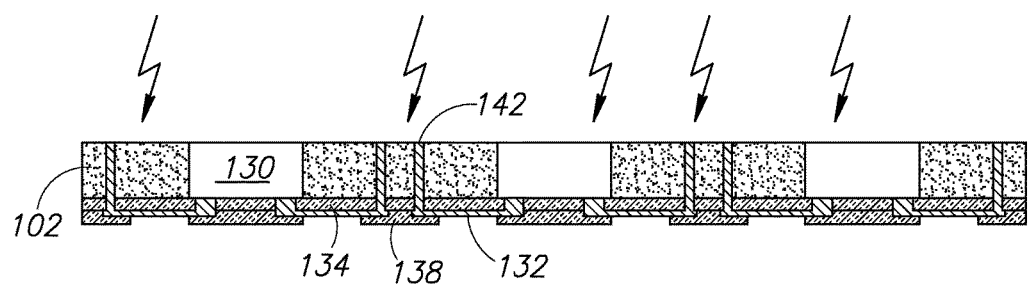
Figure 4C:
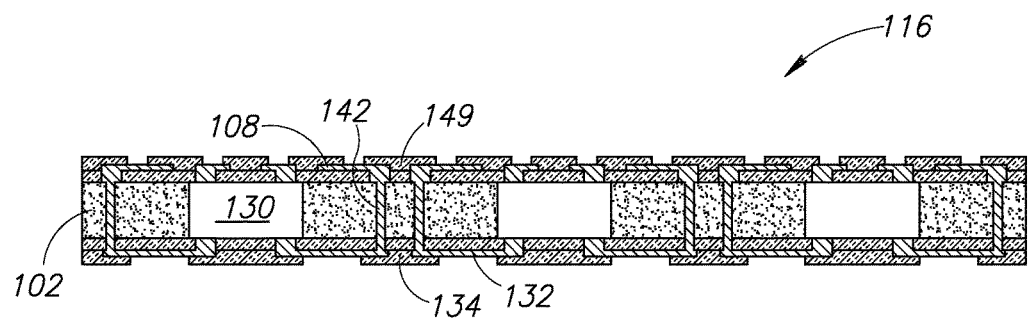

FIG. 3 shows generalized steps in a method 120 of fabricating the compact microelectronic integrated gas sensor packages 116 and 118. FIGS. 4A, 4B, and 4C show cross-sectional views of the substrate 102 at various stages of the method 120. The method 120 entails treating both the upper and lower surfaces of the substrate 102.

With reference to FIGS. 3, 4A, 4B, and 4C, at 122, a metal interconnect structure is formed on top and bottom surfaces of the substrate 102, according to one embodiment. The interconnect structure includes the sensor electrodes 108, top side contacts 117a, and/or bottom side contacts 117b, as shown in the examples in FIGS. 2A and 2B. The interconnect structure includes embedded circuitry that desirably incorporates one or more ASICs 130. In one embodiment, the substrate 102 is made of a molding compound. The ASIC 130 can include, for example, a microprocessor that is programmed to receive, via the sensor electrodes 108, electrical signals characteristic of a gas species under test, and to determine information about the selected gas species from the electrical signals thus acquired. The metal interconnect structure includes bottom side contacts 117b that are coupled to the ASICs 130 and are otherwise separated from the substrate 102 by a first insulator 134. A second insulator 138 covers the bottom side contacts 117b. Openings in the second insulator 138 are formed to allow contact to the bottom side contacts 117b for electrical coupling to the ASICs 130 (FIG. 4A).

At 124, the substrate 102 bearing the interconnect structure is inverted so that the metal interconnect structure just formed is on the lower surface of the substrate 102.

At 126, vias 142 are formed in the substrate 102 (FIG. 4B). The vias 142 extend from the upper surface of the substrate 102 through to the bottom side contacts 117b on the lower surface of the substrate 102. The vias 142 are formed by removing substrate material to form via openings, filling the via openings with metal, and planarizing the top surface. Via openings in the substrate 102 can be etched, or the substrate material can be removed using a laser beam, for example.

At 128, the sensor electrodes 108 are formed in a second metal layer on the now upper surface of the substrate 102. A top side insulator 147 separates the sensor electrodes 108 from the substrate 102. A second insulator 149 provides cover of the sensor electrodes 108 at selected locations. FIG. 4C shows a cross-sectional view of the completed compact microelectronic integrated gas sensor package 116.

After the compact microelectronic integrated gas sensor package 116 is formed, different embodiments of an integrated gas sensor device can be made by adding a cap, a gas sensing compound, and a lid in different configurations. The gas sensing compound is capable of detecting one or more gas species, depending on its chemistry. Four such configurations are illustrated below, in FIGS. 6D, 7, 8, and 9. Each configuration includes a slightly different embodiment of the compact microelectronic integrated gas sensor package 116, labeled as 116a, 116b, 116c, and 116d, respectively.

Figure 5:
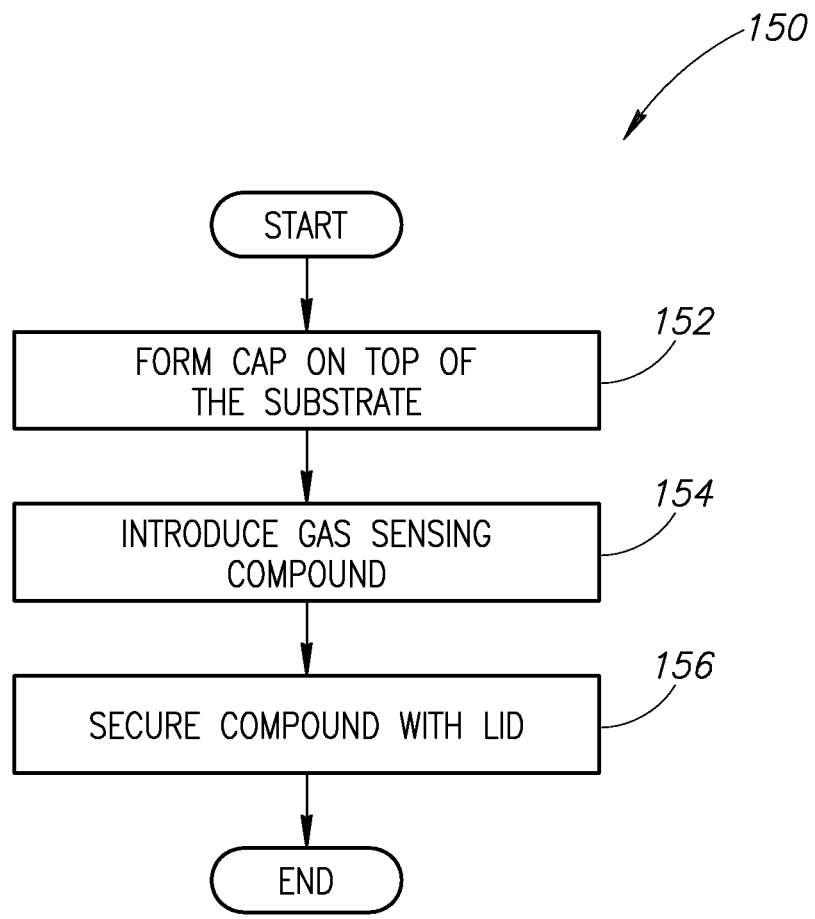
FIG. 5 is a high-level flow diagram summarizing a method of assembling a compact microelectronic gas sensor package according to one embodiment.

FIG. 5 shows a sequence of generalized steps in a method 150 of forming an integrated gas sensor device 165a according to a first embodiment. The completed integrated gas sensor device 165a is shown in FIG. 6D. FIGS. 6A, 6B, 6C, and 6D illustrate the integrated gas sensor device 165a at various stages during fabrication according to the method 150.

Figure 6A:
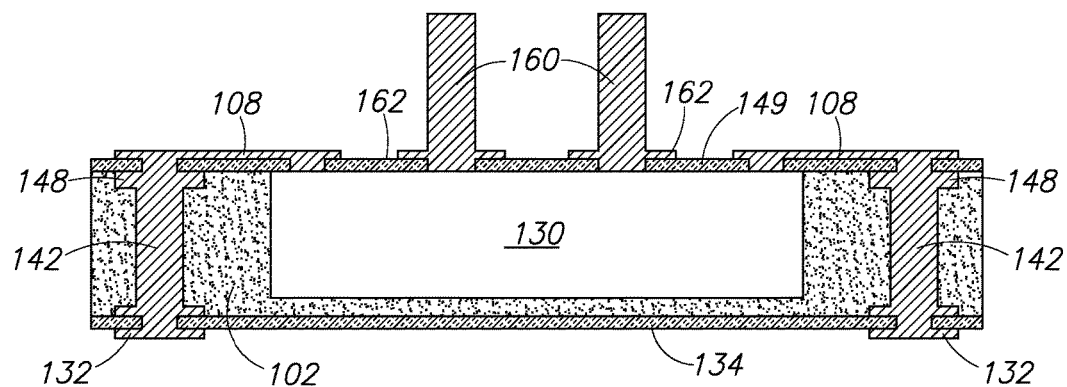
FIGS. 6A-6D are cross-sectional views of a compact microelectronic gas sensor package at various stages of fabrication, according to one embodiment.
Figure 6B:
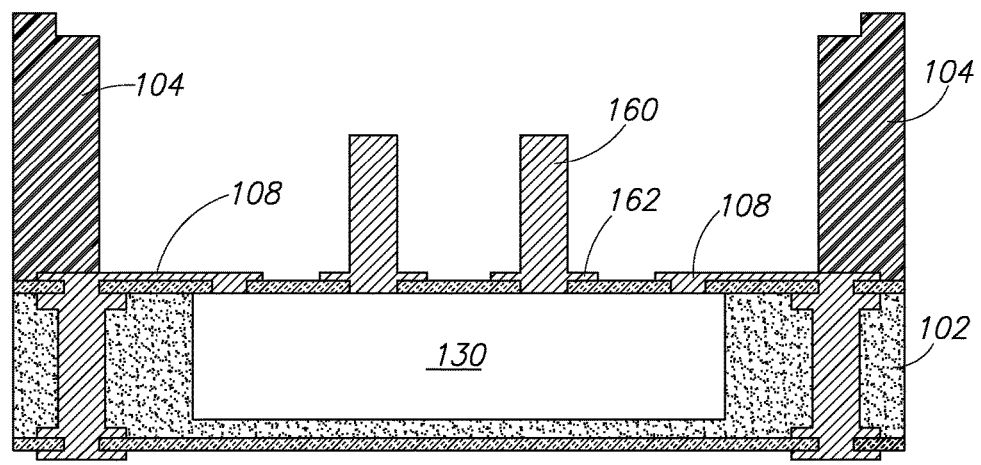

FIG. 6A shows one embodiment of the integrated gas sensor package 116 in cross section. The ASIC 130 can receive sensor signals directly from the sensor electrodes 108. In addition, metal pillars 160 are provided that extend upward into the cap 104, as shown in FIG. 6B The metal pillars 160 act as additional sensor electrodes that provide signals to the ASIC 130. Once the sensor signals are received and processed by the ASIC 130, sensor data can be accessed via a metal layer 148 in the substrate 102 or signals can be output to bottom side contacts 117b formed on the lower surface of the substrate 102. The bottom side contacts 117b are coupled to the metal layer 148 by the vias 142.

At 152, the cap 104 is formed on top of the substrate 102, extending above the upper surface. FIG. 6B shows the integrated gas sensor device 165a after attaching the cap 104. In one embodiment, the cap 104 is made of a polymer material.

Figure 6C:
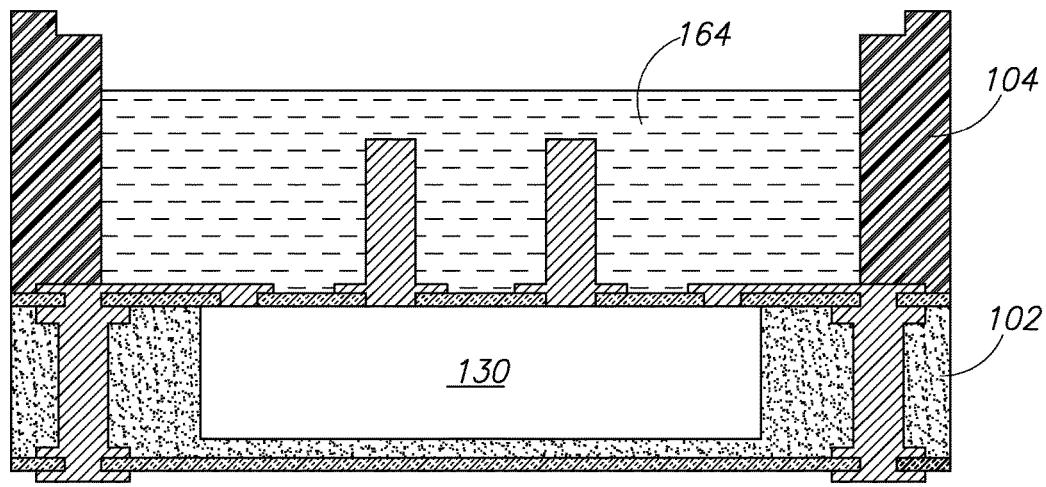
Figure 6D:
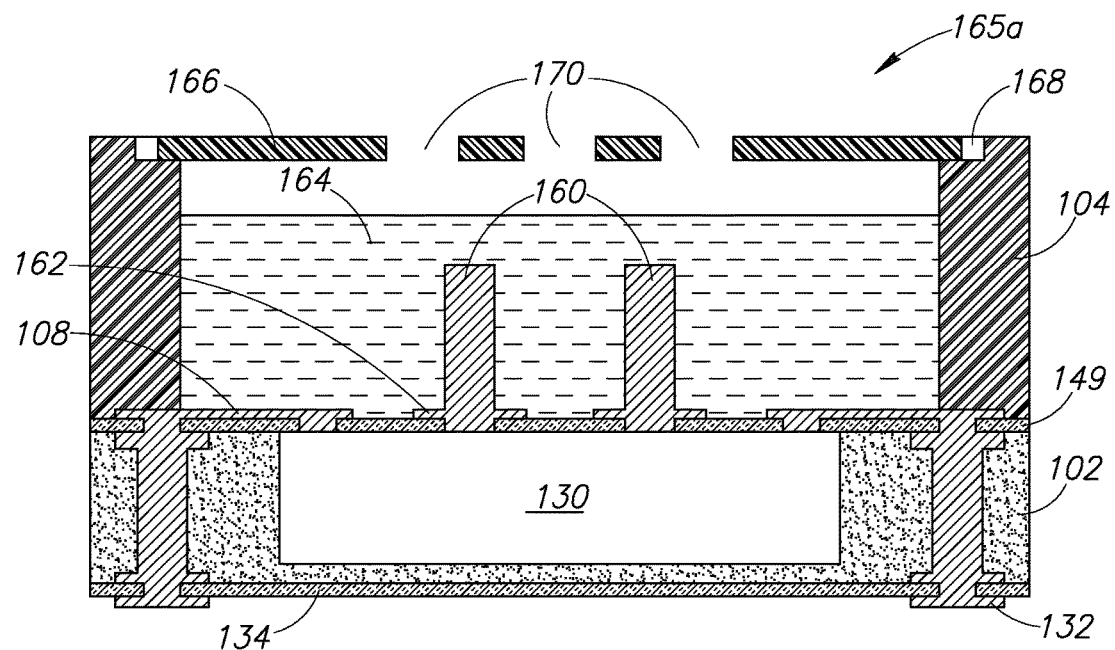

At 154, a chemireactive gas sensing compound 164 is introduced into the volume contained by the cap 104, above the ASIC 130. In one embodiment, the chemireactive gas sensing compound 164 is a gel that includes a reaction agent that changes resistivity in response to reacting with a gas species such that the change in resistivity influences an electric current in the sensor electrode 108. In this way, the sensor electrode 108 acquires charge from the chemireactive gas sensing compound 164 in response to the presence of the gas species, thus closing a sensor circuit coupled to the sensor electrode 108. In the embodiment shown in FIGS. 6A-6D, sensor electrodes 108 are coupled directly to the ASIC 130. The chemireactive gas sensing compound 164 can be dispensed as a liquid and then cured to form a gel by heating to a temperature in the range of about 80 C-100 C for about 30-60 minutes. FIG. 6C shows the compact microelectronic integrated gas sensor device 165a after introducing the chemireactive gas sensing compound 164.

The metal pillars 160 in contact with the chemireactive gas sensing compound 164 are formed, for example, by electroplating. The metal pillars 160 are coupled to the ASIC through pillar contacts 162 formed as part of the integrated gas sensor package 116. The metal pillars 160 provide additional metal surface area exposure, in addition to that of the sensor electrodes 108, for sensing changes in the chemireactive gas sensing compound 164 as reactions with various gas species occur. The metal pillars 160 thus can be considered extensions of the sensor electrodes 108. Accordingly, the metal pillars 160 are desirably made of a high conductivity material, the same as or similar to the material used to form the sensor electrodes 108. The additional surface area provided by the metal pillars 160 offers more opportunity to sense changes in electrical conductivity of the chemireactive gas sensing compound 164, and thus improves accuracy of the compact microelectronic integrated gas sensor device 165a. The largest electrical signal enhancement will occur when the metal pillars 160 are immersed in the chemireactive gas sensing compound 164. Electrical signals sensed by the chemireactive gas sensing compound 164 can be accessed by connections to either the top side electrical contacts 117a on the top surface of the substrate 102 or by connections to the bottom side contacts 117b on the bottom surface of the substrate 102.

At 156, the chemireactive gas sensing compound 164 is secured by attaching a lid 166 to the cap 104. The lid 166 covers the chemireactive gas sensing compound 164. Openings 170 in the lid 166 permit entry of ambient gas species into the cap 104 to be sensed by the chemireactive gas sensing compound 164. FIG. 6D shows the completed the compact microelectronic integrated gas sensor device 165a after attaching the lid 166 to the top of the cap 104. The lid 166 encloses the chemireactive gas sensing compound 164 and head space 172 above the surface of the chemireactive gas sensing compound 164. Thus, the lid 166, together with the cap 104 and the top surface of the package 116 thus provide a container for the chemireactive gas sensing compound 164. The lid 166 is secured with an adhesive 168 such as, for example, an epoxy that is cured using ultraviolet light.

Figure 7:
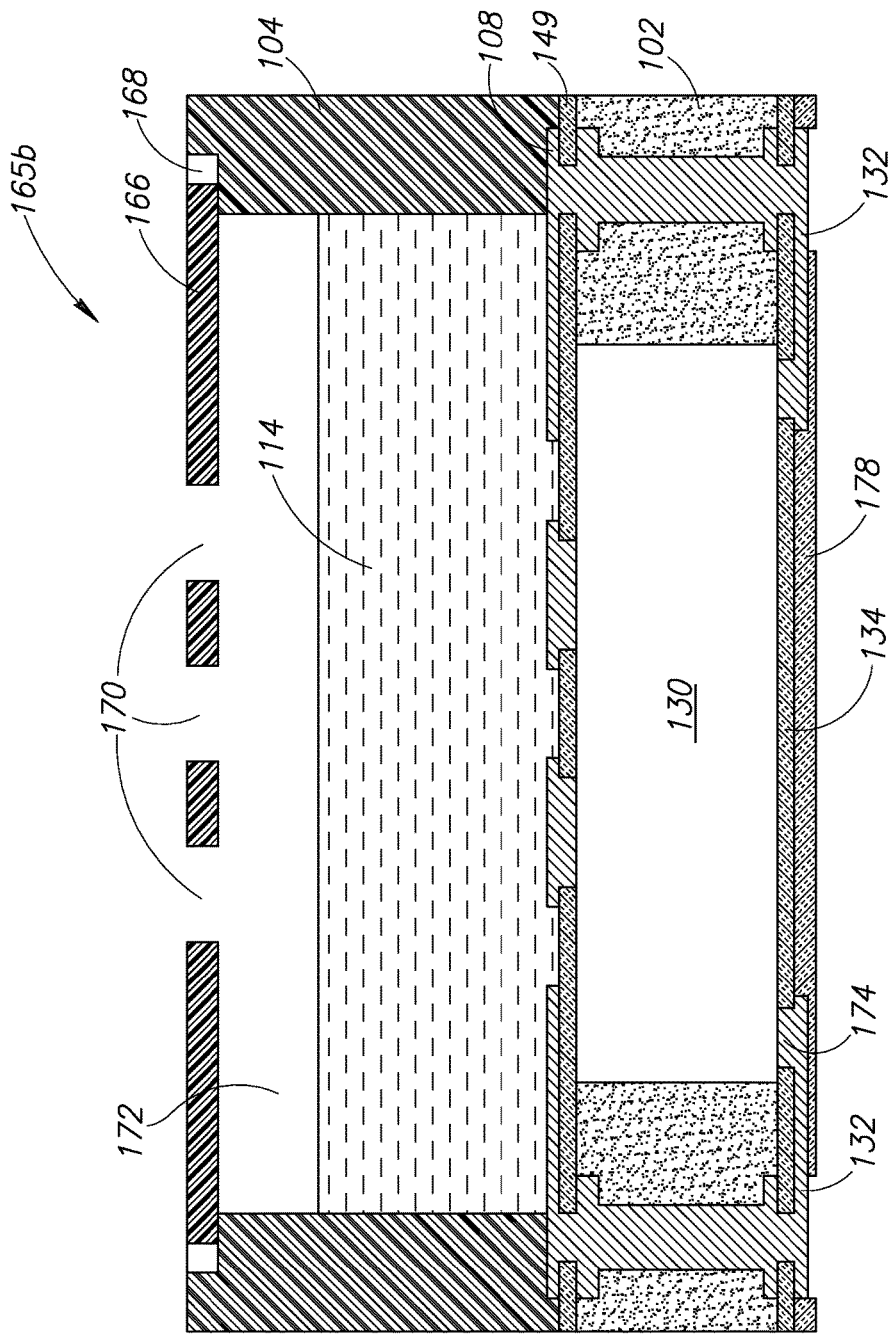
FIG. 7 is a cross-sectional view of a compact microelectronic gas sensor package according to a second embodiment.

FIG. 7 shows a second embodiment of a compact microelectronic integrated gas sensor device, 165b. The integrated gas sensor device 165b does not include the metal pillars 160. Signals from the gas sensor electrodes 108 that are in contact with the chemireactive gas sensing compound 164 are transmitted through the vias 142 to the bottom side contacts 117b and to the ASIC 130 through back side contacts 174. An additional insulating layer 178 protects the bottom side contacts 117b. The embodiments shown in FIGS. 6D and 7, which feature an embedded ASIC, have the additional advantage that no wire bonds or bumps are used in packaging the ASIC. Instead, such connection points are built into the integrated gas sensor package 116.

Figure 8:
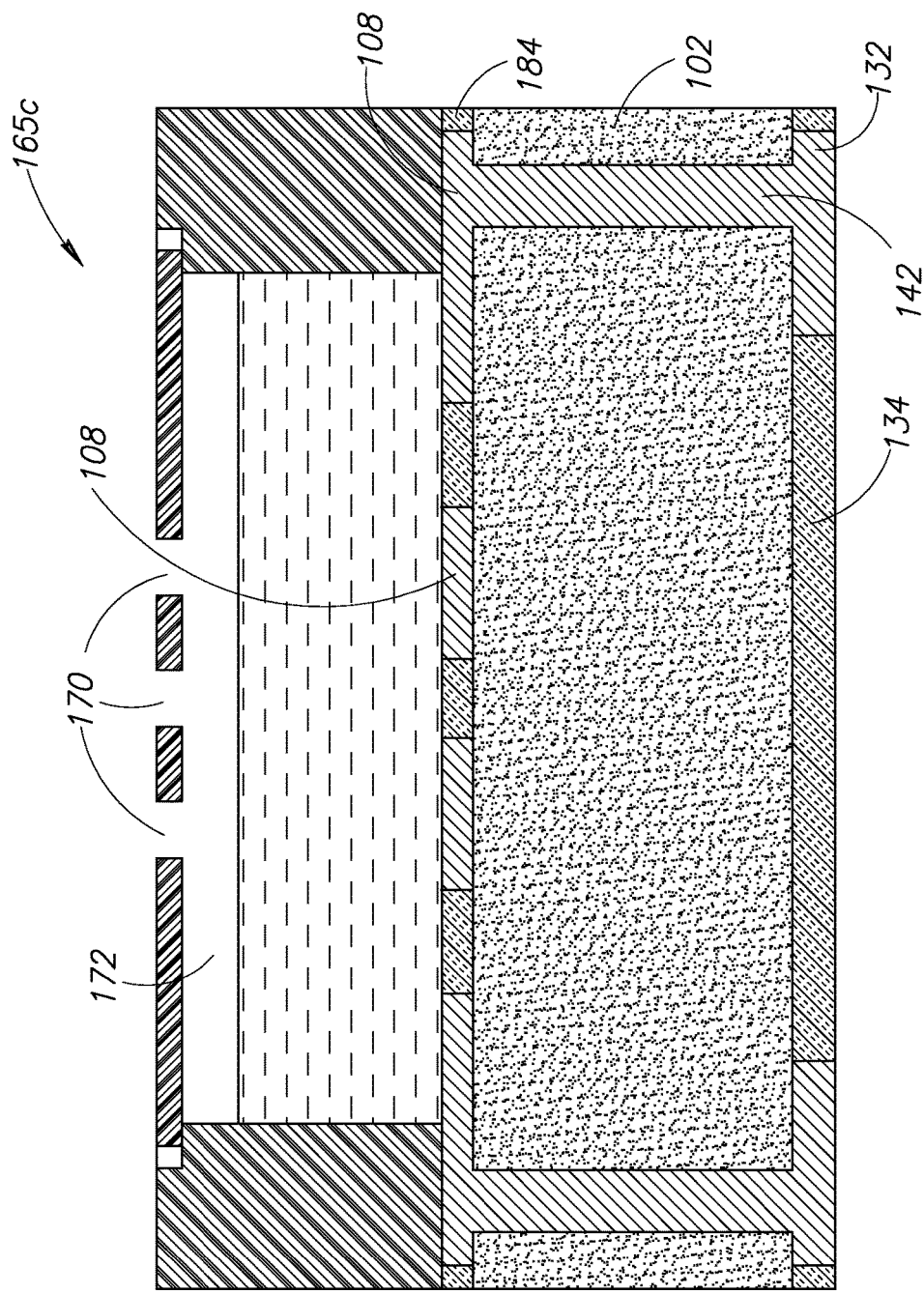
FIG. 8 is a cross-sectional view of a compact microelectronic gas sensor package according to a third embodiment.

FIG. 8 shows a third embodiment of a the compact microelectronic integrated gas sensor device, 165c. The integrated gas sensor device 165c omits embedded circuitry in the form of a built-in ASIC. The ASIC or other processing circuitry is located adjacent to, or otherwise apart from the integrated gas sensor device, 165c. Furthermore, the structure of the integrated gas sensor package 116 is simplified to include only the basic parts. Because the ASIC is distanced from the chemireactive gas sensing compound 164, more of the upper metal layer can be used as gas sensor electrodes 108.

Figure 9:
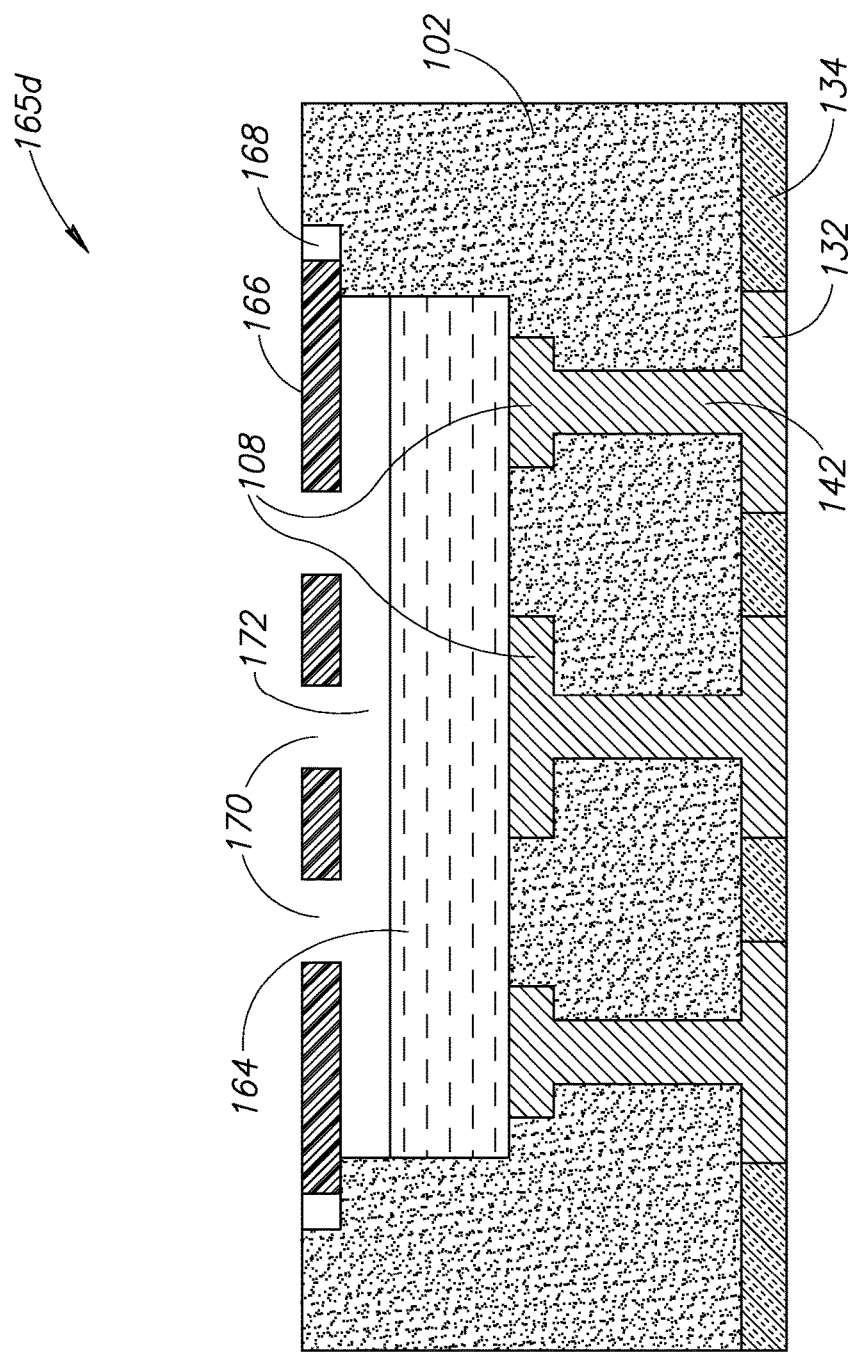
FIG. 9 is a cross-sectional view of a compact microelectronic gas sensor package according to a fourth embodiment.

FIG. 9 shows a fourth embodiment of a compact microelectronic gas sensor package, 165d. The compact microelectronic gas sensor package 165d omits embedded circuitry in the form of a built-in ASIC. Like the integrated gas sensor device, 165c, the structure of the integrated gas sensor package 116 is simplified to include only the basic parts. Furthermore, the integrated gas sensor device 165d excludes the cap 104. Instead of employing the cap 104 to accommodate the chemireactive gas sensing compound 164, head space 172, and lid 166, such elements are contained in a cavity formed within the substrate 102 such that the walls of the substrate 102 perform the function of the cap 104. The cavity is therefore partially filled with the chemireactive gas sensing compound 164. Again, the surface area of the gas sensor electrodes 108 can be enlarged because the ASIC is not embedded locally and therefore contacts to the ASIC are not needed.

Figure 10:
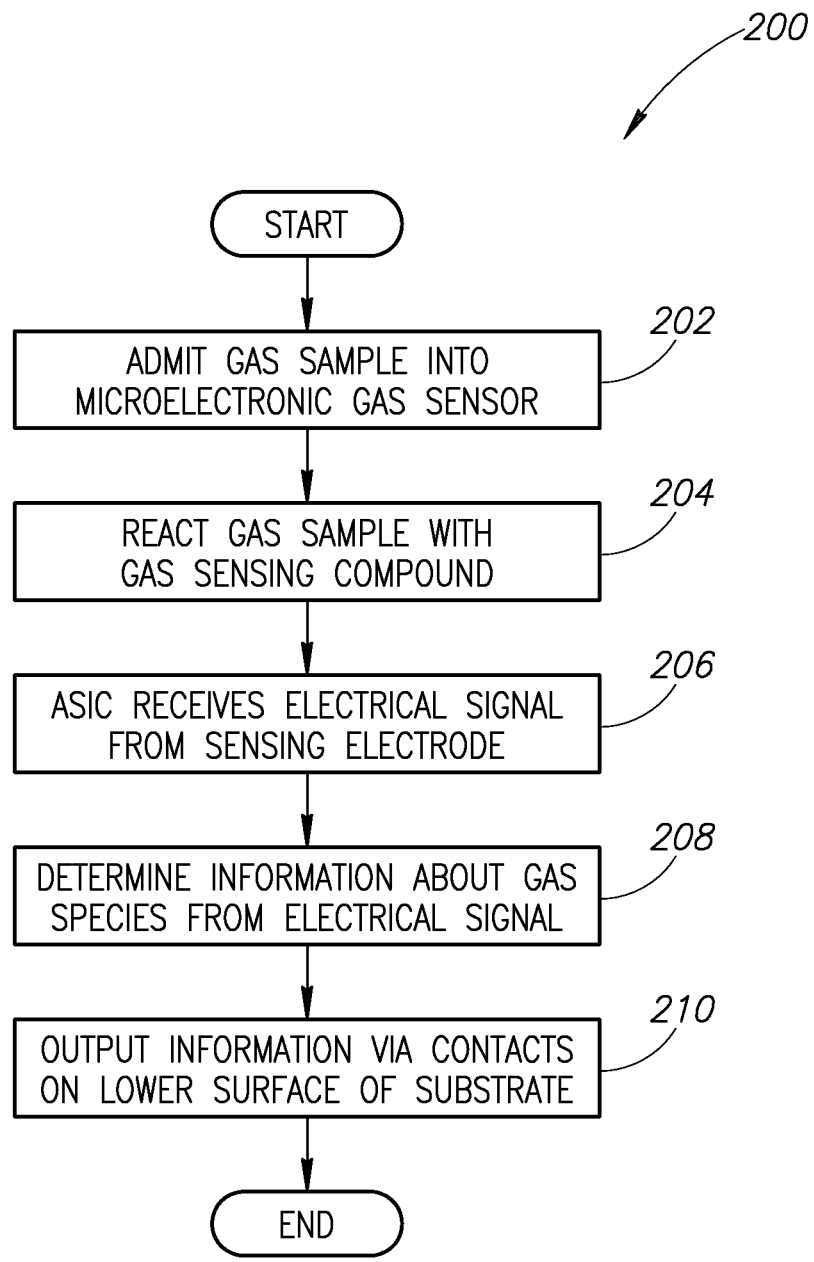
FIG. 10 is a process flow diagram showing a sequence of steps in a method of operating a compact microelectronic gas sensor package, according to one embodiment.

FIG. 10 shows generalized steps in a method 200 of operating a microelectronic integrated gas sensor device having contacts to the bottom side contacts 117b, e.g., any one of the embodiments 165a, 165b, 165c, or 165d, collectively 165.

At 202, a gas sample is admitted into the integrated gas sensor device 165 via the openings 170.

At 204, the gas sample reacts with the gas sensing compound 164 to produce an electric current in the sensor electrode 108. The electric current in the sensor electrode 108 closes a sensor circuit and transmits electric current from the gas sensing compound to the ASIC 130.

At 206, the ASIC 130 receives an electrical signal from the sensor electrode 108 that indicates that a change has occurred in the current at the sensor electrode 108. The electrical signal may be received directly from the sensor electrode 108, or through the vias 142.

At 208, the ASIC determines information about one or more gas species present in the gas sample by analyzing the electrical signal received from the sensor electrode 108. The determined information can include, for example, identification of the gas species, concentration of certain chemical elements or compounds, and the like.

At 210, the information determined about the one or more gas species is provided as an output signal at the bottom side contacts 117b on the lower surface of the substrate 102.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

It will be appreciated that, although specific embodiments of the present disclosure are described herein for purposes of illustration, various modifications may be made without departing from the spirit and scope of the present disclosure. Accordingly, the present disclosure is not limited except as by the appended claims.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device, comprising:
   a substrate having a first surface and a second surface opposite to the first surface;
   a cap overlying the first surface of the substrate, the cap configured to contain a chemireactive gas sensing compound;
   a sensor electrode on the first surface of the substrate, the sensor electrode having a metal surface area exposed to the chemireactive gas sensing compound, the sensor electrode operable to close a sensor circuit upon acquiring an electric charge from the gas sensing compound in response to presence of a gas species;
   contacts formed on the second surface of the substrate;
   conductive vias that electrically couple the contacts to the sensor electrode and extend between the first surface and the second surface of the substrate; and
   a lid attached to the cap, the lid covering the chemireactive gas sensing compound and having one or more openings therein that permit entry of the gas species into the cap.

2. The device of claim 1, further comprising circuitry embedded in the substrate and communicatively coupled to the sensor electrode.

3. The device of claim 2 wherein the embedded circuitry includes an application specific integrated circuit (ASIC) programmed to determine information about the gas species from an electrical signal acquired by the sensor electrode.

4. The device of claim 2 wherein the embedded circuitry is coupled to the sensor electrode through the vias.

5. The device of claim 2 wherein the embedded circuitry is wired directly to the sensor electrode.

6. The device of claim 1 wherein the contacts extend below the second surface of the substrate.

7. The device of claim 1 wherein the sensor electrode further includes a metal pillar extending from the first surface of the substrate to the lid, the metal pillar providing an additional metal surface area exposed to the gas sensing compound.

8. The device of claim 7 wherein the metal pillar is immersed in the gas sensing compound.

9. The device of claim 1 further comprising additional contacts formed on the first surface of the substrate, the additional contacts coupled directly to the sensor electrodes.

10. The device of claim 1 wherein the gas sensing compound is an electrolyte.

11. A method comprising:
forming a cap over a first surface of a substrate, the cap configured to contain a chemireactive gas sensing compound;
forming a sensor electrode on the first surface of the substrate, the first surface having a metal surface area exposed to the chemireactive gas sensing compound, the sensor electrode operable to close a sensor circuit upon acquiring an electric charge from the gas sensing compound in response to presence of a gas species;
forming contacts on a second surface, opposite to the first surface, of the substrate;
forming conductive vias that electrically couple the contacts to the sensor electrode and extend between the first surface and the second surface of the substrate; and
attaching a lid to the cap, the lid covering the chemireactive gas sensing compound and having one or more openings therein that permit entry of the gas species into the cap.

12. The method of claim 11 wherein the substrate is made of a molding compound.

13. The method of claim 11 wherein the substrate includes an integrated circuit die.

14. A device, comprising:
a substrate having a first surface and a second surface opposite to the first surface;
a container overlying the first surface of the substrate and configured to hold a chemireactive gas sensing compound;
a plurality of sensor electrodes on the first surface of the substrate, the plurality of sensor electrodes configured to be exposed to the chemireactive gas sensing compound and read electrical currents produced by the chemireactive gas sensing compound;
a plurality of contacts on the second surface of the substrate; and
a plurality of conductive vias electrically coupling the plurality of sensor electrodes to the plurality of contacts.

15. The device of claim 14, further comprising a plurality of conductive pillars on the first surface of the substrate and extending in to the container, the plurality of conductive pillars configured to be exposed to the chemireactive gas sensing compound and read the electrical currents produced by the chemireactive gas sensing compound.

16. The device of claim 15, further comprising an integrated circuit in the substrate, the plurality of sensor electrodes being spaced from the plurality of contacts by the integrated circuit, the integrated circuit being electrically coupled to at least one of the plurality of sensor electrodes and at least one of the plurality of contacts.

17. The device of claim 14, further comprising:
a first insulator layer on the first surface of the substrate, the plurality of sensor electrodes extending through the first insulator layer; and
a second insulator layer on the second surface of the substrate, the plurality of contacts extending through the second insulator layer.

18. The device of claim 14 wherein the container includes:
a cap attached the first surface on the substrate; and
a lid attached the cap, the lid having a plurality of openings that expose the chemireactive gas sensing compound to an environment outside of the container.

19. The device of claim 14 wherein the container includes:
sidewalls that are formed by portions of the substrate; and
a lid on the sidewalls, the lid having a plurality of openings that expose the chemireactive gas sensing compound to an environment outside of the container.

* * * * *